US012582540B2

(12) United States Patent
Castillo Suescún et al.

(10) Patent No.: US 12,582,540 B2
(45) Date of Patent: Mar. 24, 2026

(54) INTRAGASTRIC DEVICE

(71) Applicants:SERVICIO CÁNTABRO DE SALUD, Santander (ES); UNIVERSIDAD DE CANTABRIA, Santander (ES)

(72) Inventors: Federico Castillo Suescún, Santander (ES); Javier Crespo García, Santander (ES); Juan Carlos Rodríguez Sanjuan, Santander (ES); Ramón Sancibrián Herrera, Santander (ES)

(73) Assignee: Servicio Cántabro De Salud Universidad De Cantabria, Santander (ES)

( * ) Notice: Subject to any disclaimer, the term of this patent is extended or adjusted under 35 U.S.C. 154(b) by 98 days.

(21) Appl. No.: 18/577,478

(22) PCT Filed: Jul. 6, 2022

(86) PCT No.: PCT/ES2022/070433
§ 371 (c)(1),
(2) Date: Jan. 8, 2024

(87) PCT Pub. No.: WO2023/281147
PCT Pub. Date: Jan. 12, 2023

(65) Prior Publication Data
US 2025/0017752 A1 Jan. 16, 2025

(30) Foreign Application Priority Data
Jul. 9, 2021 (ES) ............................... ES202130649

(51) Int. Cl.
*A61F 5/00* (2006.01)
(52) U.S. Cl.
CPC .......... *A61F 5/0036* (2013.01); *A61F 5/0083* (2013.01)

(58) Field of Classification Search
CPC .... A61F 5/0036; A61F 5/0083; A61F 5/0043; A61F 5/0076; A61F 5/0033
See application file for complete search history.

(56) References Cited

U.S. PATENT DOCUMENTS 4,416,267 A 11/1983 Garren et al.
4,694,827 A 9/1987 Weiner et al.
(Continued)

FOREIGN PATENT DOCUMENTS

ES 2349007 T3 12/2010
ES 2562035 3/2016
FR 2892297 B1 3/2010

OTHER PUBLICATIONS

International Search Report and Written Opinion of the ISA/ES dated Oct. 4, 2022 in International Application No. PCT/ES2022/070433; 19pgs.

*Primary Examiner* — Richard G Louis
(74) *Attorney, Agent, or Firm* — Haukaas Fortius PLLC; Michael Haukaas

(57) ABSTRACT

Intragastric device intended to be inserted into a gastric cavity to restrict its capacity. To contribute to optimal adaptation, its design is based on the principle of neutral buoyancy. The device comprises an inner core and an outer covering (2). The inner core consists of a closed chamber (1) and a first valve (4) connecting the inside of the chamber (1) to the outside, through which a pressurised fluid is introduced into the chamber (1). The outer covering (2) comprises a first cavity (5), in which the core is housed, and a second valve (7), through which a volume of fluid is introduced into the free space of the cavity not occupied by the chamber (1). This fluid in the first cavity (5) is at a different pressure to that of the fluid introduced into the chamber (1).

17 Claims, 9 Drawing Sheets

(56) References Cited

U.S. PATENT DOCUMENTS

| | | |
|---|---|---|
| 4,739,758 A | 4/1988 | Lai et al. |
| 2016/0095731 A1 | 4/2016 | Connor et al. |

9

INTRAGASTRIC DEVICE

RELATED APPLICATIONS

This application is a National Stage filing under 35 U.S.C. § 371 of International Application No. PCT/ES2022/070433 filed Jul. 6, 2022, which claims the benefit of Spain Application No. P202130649 filed Jul. 9, 2021, which applications are incorporated herein by reference.

OBJECT OF THE INVENTION

The present invention falls within the technical field of orthopaedic devices for non-surgical treatment, more specifically devices specially designed to be inserted, deployed, inflated and monitored inside the gastric cavity for the treatment of obesity, and refers in particular to an intragastric device.

BACKGROUND TO THE INVENTION

Obesity has become a growing public health problem. According to the World Health Organisation, obesity has almost tripled worldwide since 1975 and in 2016, more than 1.9 billion adults over the age of 18 were overweight, of which more than 650 million were obese. Except in pathological cases, weight gain is directly related to overeating.

Treatment of obesity should be comprehensive and multidisciplinary to achieve and maintain a healthy weight. Initial treatment of obesity includes changes in dietary patterns and increased physical exercise. In addition to these strategies, and depending on the degree of obesity, drugs may be administered, or bariatric surgery may be chosen to enhance weight loss. Surgery is one of the most effective treatments, but its approach remains empirical and not without complications and sequelae. On the other hand, there are a variety of endoscopic techniques to try to control satiety by acting on the digestive tract and, in particular, on the stomach. Among them, the intragastric balloon is still the most widely used and one of the most effective in terms of restrictive techniques.

This intragastric balloon treatment involves inserting a balloon made of medical silicone, among other materials, into the stomach endoscopically. This balloon is predominantly filled with a solution so that it can produce a limitation in stomach capacity and help the patient to modify their eating habits and, therefore, change their lifestyle. When the intragastric balloon is placed, the sensation of hunger decreases, and satiety increases. As a result, there is a weight reduction in a short time.

Various intragastric devices and balloons for treating obesity are known in the current state of the art. For example, documents U.S. Pat. Nos. 4,416,267, 4,694,827 and 4,739,758, refer to intragastric balloons that are inflated inside a gastric cavity occupying a substantial part of its volume to discourage food intake. These devices can be introduced by endoscopic techniques.

In particular, U.S. Pat. No. 4,416,267 describes a toroid-shaped flexible inflatable balloon comprising a central opening extending through the balloon. The central opening provides a passageway for solids and liquids as they pass through the abdominal cavity. The central opening includes outer ends that provide a wide entrance to the central opening.

Document U.S. Pat. No. 4,694,827 refers to a balloon that can be inserted and inflated inside the stomach to discourage food intake. Once inflated, the balloon has a plurality of smooth-surfaced convex protrusions arranged in such a way as to allow coupling between the stomach wall and the balloon only at spaced locations to minimise mechanical trauma to the abdominal wall.

U.S. Pat. No. 4,739,758 features a balloon composed of 2 layers of material; the outer layer is a thin film of silicone rubber, and the inner layer consists of a thicker film of more durable, low gas permeable EVA or other durable, low gas permeable polymer such as butyl or urethane. The inflated balloon has a plurality of blisters on its surface. These blisters prevent the balloon from sitting tightly against the cardia or pylorus and thus allow food to pass through it. The blisters on the outer surface of the balloon allow digested food to pass safely around the balloon through the duodenum.

Despite the various intragastric balloon options available in the state of the art, these devices continue to cause intolerance, nausea, vomiting, abdominal pain, as well as risk of erosions and ulcers. In addition, effectiveness problems are commonly caused by inadequate inflation levels, which obstruct the passage of food rather than restricting it, which is what these devices are intended to do.

On the other hand, document ES2349007T3 describes an intragastric balloon for the treatment of obesity, intended to be implanted in the stomach of a patient to reduce the volume of the stomach, the balloon comprising a flexible envelope delimiting a predetermined internal volume, said flexible envelope being made of an elastomeric material. The dimensional tolerance of the nominal thickness of the envelope is between 1% and 20%.

ES2562035T3 describes an intragastric implant for the treatment of obesity, comprising:

an outer inflatable balloon configured to be disposed in the stomach of a patient, wherein the outer inflatable balloon is configured to be inflated with saline after implantation in the stomach of the patient and having a length oriented along a longitudinal axis substantially spanning the stomach such that a first end of the implant is positioned adjacent to the antrum and a second end of the implant is positioned adjacent to the cardia; and a central balloon located within the outer inflatable balloon is adapted to contain air without leakage to occupy volume within the outer inflatable balloon, wherein the central balloon includes a top portion that is housed within the second end of the outer balloon, characterised by a lower part that is housed within the first end of the outer balloon that has a smaller internal volume than the upper part so that the greater buoyancy of the upper part tends to orient the second end of the outer balloon in the upper part of the stomach cavity adjacent to the cardia.

Finally, US2016095731A1 discloses an expandable intragastric device for reducing food consumption and/or absorption. In one example, this device can be incorporated into a plurality of longitudinal expandable members that are arranged in a colonnade configuration to form a restrictive lumen for food within a stomach. Pumping a fluid substance between the interiors of these expandable members changes the rate of flow of food through the stomach, the ability of the stomach to hold food and/or the amount of food absorbed by the body. This offers some of the beneficial effects of gastric sleeve surgery, as well as being adjustable and reversible.

However, the devices shown in these documents still present problems of adaptation to the user's anatomy, as their elements are mainly rigid. There is therefore a need for an intragastric device that overcomes all the drawbacks of the current state of the art.

DESCRIPTION OF THE INVENTION

The object of the invention consists of an intragastric device intended to be introduced inside a gastric cavity to restrict its capacity, and thus help to treat severe weight imbalances by reducing food intake.

Since the intragastric device is to be inserted in a liquid medium, in order to reduce its weight and thus contribute to optimal adaptation, its design is based on the principle of neutral buoyancy. Neutral buoyancy occurs when the density of an object is equal to the density of the fluid in which it is immersed, resulting in a buoyant force that balances the force of gravity. Thus, an object that is neutrally buoyant will neither sink nor rise and will also be lighter in weight.

The device comprises a flexible, hollow inner core and a flexible outer covering that surrounds and contains the inner core. All the elements that make up the intragastric device are made of biocompatible materials.

The inner core consists of a closed chamber and a valve that connects the inside of the chamber to the outside, through which a pressurized fluid is introduced into and extracted from the closed chamber. The outer covering comprises an internal cavity, which houses the core, and a respective valve, through which a volume of fluid is introduced into and extracted from the cavity into the free space not occupied by the chamber. This fluid is introduced at a different pressure, preferably lower than that of the fluid introduced into the chamber.

By regulating the volumes of fluid at different pressures inside the core and the covering respectively, the total volume occupied by the device inside the gastric cavity is adapted. The result is an intragastric device with an internal chamber in which a pressurized fluid is housed and which generates a resistance to prevent the device from entering the intestine. At the same time, the fluid housed in the external chamber, with a different pressure to that of the internal chamber, avoids the complications caused by obstruction that occur in other intragastric balloons.

According to a preferred embodiment of the device, the covering incorporates inflatable and deflatable external thickenings intended to increase the contact surface with the walls of the gastric cavity. These thickenings can have different geometries, including bubbles, helixes, or spirals, and also help to prevent the device from sticking to the walls of the gastric cavity.

In a preferred embodiment of the device, the inner chamber of the core has one or two tapers on its walls which divide it into two or three sectors connected to each other by means of these tapers. The tapers are also points which allow a certain degree of torsion of the inner core chamber within the cladding, which helps to facilitate the adaptation of the device.

In another preferred embodiment, the covering incorporates one or two internal membranes for compartmentalization of the internal cavity, into which the core is inserted. Each of the compartments into which the internal cavity is divided is connected to its own flow inlet of the fluid inlet valve, so that the amount of fluid it contains can be regulated independently, thus facilitating control of the volume occupied by the device.

In alternative embodiments of the device, the thickenings are separated by a membrane from the internal cavity of the covering and the device incorporates a new flow inlet valve by which the amount of fluid contained in the thickenings can be regulated independently of the other elements of the intragastric device and can be inflated and deflated independently of the other elements of the intragastric device.

In alternative embodiments of the device, the inner core and outer covering are bonded together in certain areas of their surface to ensure that there is no or at least minimal displacement between the two structures.

The intragastric device thus described is a simple, effective, and economical solution to overcome the disadvantages of the current state of the art, giving rise to a device with neutral buoyancy and reduced weight, whose volume allows for a highly regulated adjustment, thus avoiding the intolerances and discomfort that are usually caused in users.

DESCRIPTION OF THE DRAWINGS

In order to complement the description being made and in order to assist in a better understanding of the features of the invention, in accordance with a preferred example of a practical embodiment thereof, a set of drawings is attached hereto as an integral part of the said description, in which the following is illustrated for illustrative and non-limiting purposes.

PREFERRED EMBODIMENT OF THE INVENTION

Figures 1, 2:
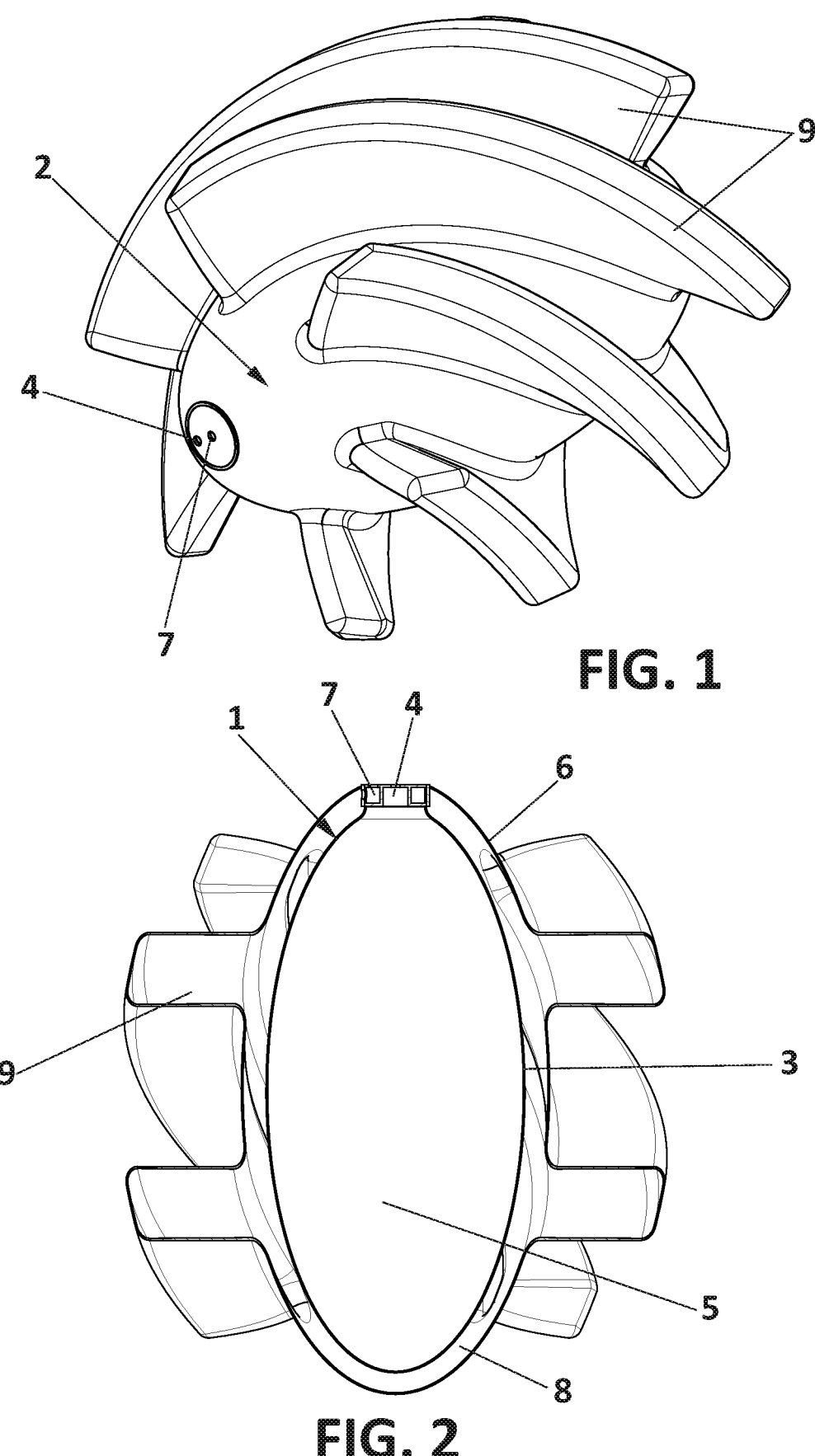
FIG. 1.—Shows a perspective view of the intragastric device according to a first preferred embodiment.
FIG. 2.—Shows a cross-section of the device in FIG. 1.

A detailed explanation of an example of a preferred embodiment of the subject matter of the present invention is given below with the aid of the figures referred to above.

The intragastric device described is intended to be inserted inside a gastric cavity to occupy part of its volume and thus restrict the capacity to ingest food. For this purpose, the device has an ellipsoidal geometry and basically consists of a flexible inner core, hereinafter referred to as chamber (1), and an outer covering (2), also flexible, which at least partially surrounds and contains the chamber (1).

The chamber (1), of ellipsoidal geometry, comprises a first wall (3), curved and closed on itself, and a first valve (4). The first wall (3) has an external face and an internal face, which perimetrically delimits a first hollow internal cavity (5). The first valve (4) passes through the first wall (3) and the covering (2) to connect the first cavity (5) to the outside of the intragastric device.

This first cavity (5) is intended to be filled, at least partially, by a volume of fluid under pressure, which is introduced and extracted through the first valve (4). This fluid may be air, water, or a saline solution, among others.

The covering (2) comprises a second wall (6), curved and closed on itself, and a second valve (7). The second wall (6) has an external face, intended to face the internal walls of the gastric cavity, and an internal face, which perimetrically delimits a second cavity (8). The second valve (7) passes through the second wall (6) to connect the second cavity (8) to the outside of the intragastric device.

The second cavity (8) houses the first wall (3) and part of the first valve (4) of the chamber (1) and is intended to be at least partially filled by a volume of fluid at a pressure different from that of the fluid in the first cavity (5). This fluid is introduced and extracted through the second valve (7) to occupy a space defined between the external face of the first wall (3) and the internal face of the second wall (6). As in the case of the first cavity (5), the fluid introduced into the second cavity (8) through the second valve (7) can be air, water, or a saline solution, among others.

In the embodiments described herein, the fluid inside the first cavity (5) has a higher pressure than the fluid inside the second cavity (8). In alternative embodiments, it is the fluid in the second cavity (8) that has a higher-pressure value than the fluid inside the first cavity (5).

Figure 3:
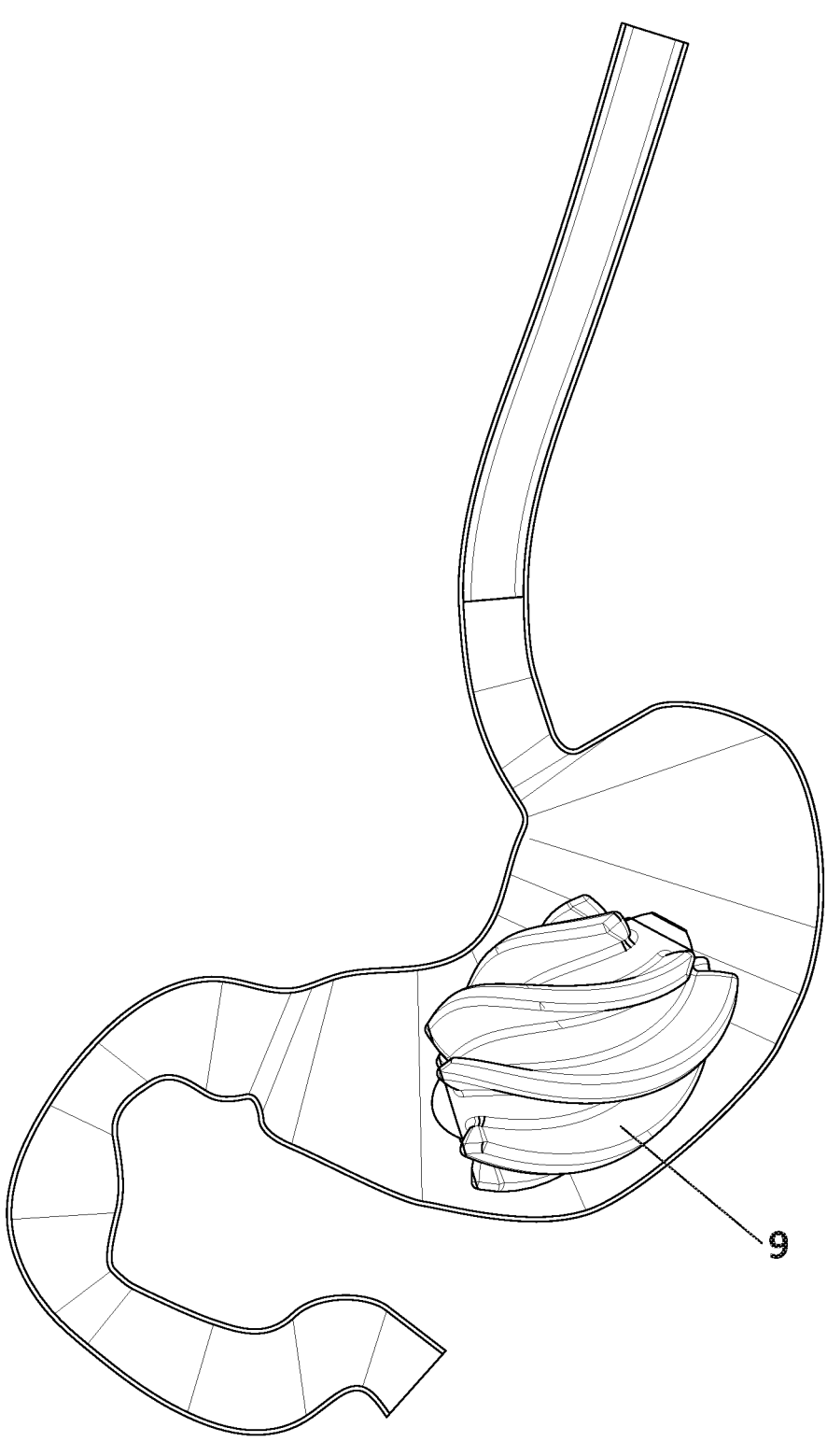
FIG. 3.—Shows the device of FIG. 1 inserted inside a gastric cavity.

FIGS. 1-3 illustrate views of the intragastric device according to a first preferred embodiment. As can be seen, in this embodiment, the covering (2) incorporates a plurality of helical thickenings (9) which, starting from the external face of the second wall (6), project outwards from the device. These helical thickenings (9), which are connected to the second cavity (8) and whose volume is therefore adjustable, help to facilitate the adaptation of the device to the interior of the gastric cavity in which it is intended to be inserted.

Figures 4, 5:
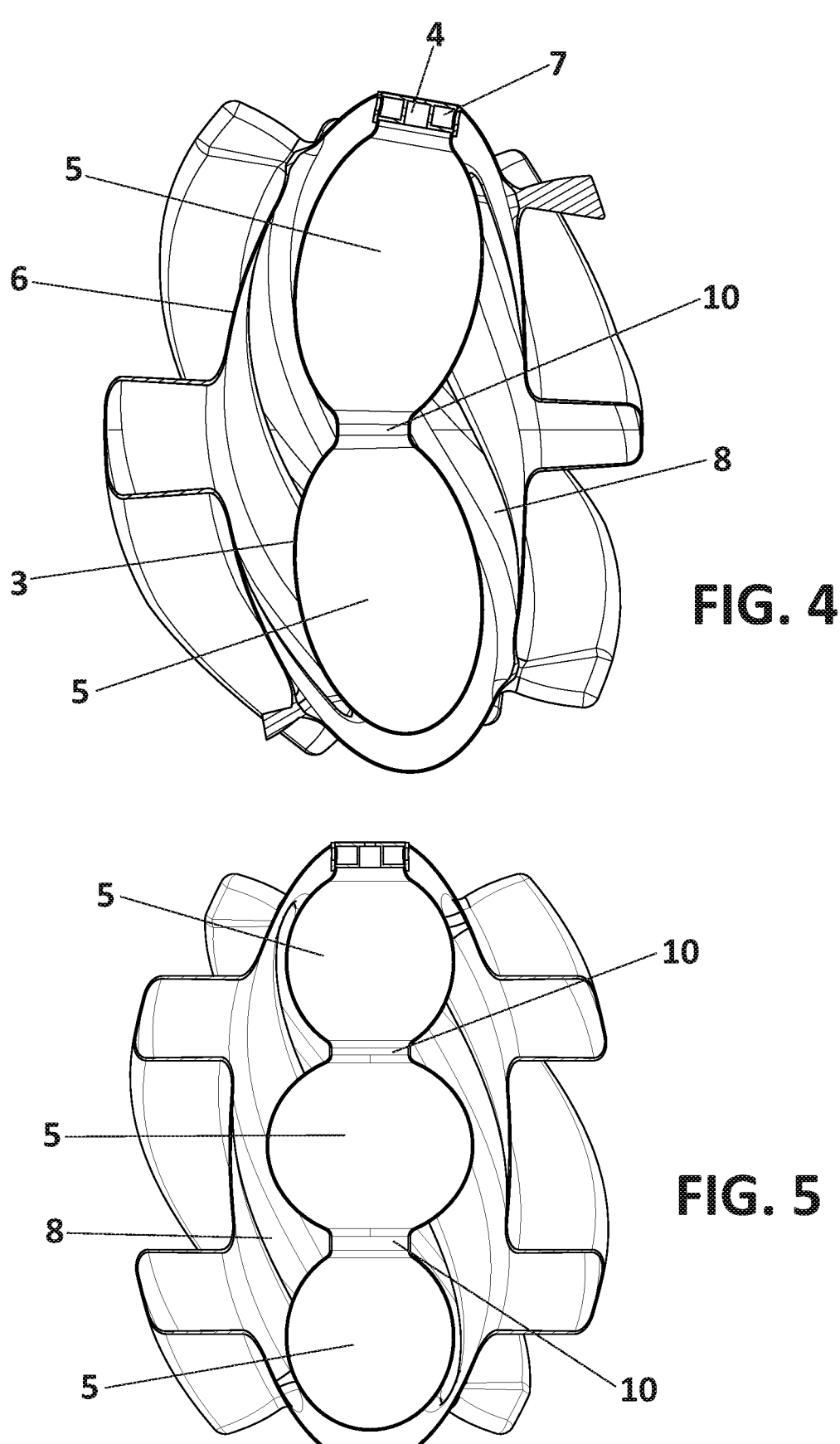
FIG. 4.—Shows a cross section of the device according to a second embodiment.
FIG. 5.—Shows a cross section of the device according to a third embodiment.

FIG. 4 shows a second embodiment of the intragastric device, in which the first internal cavity (5) of the chamber (1) is made up of two sectors connected to each other by means of a narrowing (10). As can be seen in this figure, in this case the two sectors of the first internal cavity (5) have similar dimensions and the narrowing (10) is formed by a dimensional reduction of the first wall (3).

The narrowing (10) helps to make the first wall (3) of the chamber (1) more flexible, thus facilitating adaptation to the interior of the second cavity (8) and, therefore, of the device inside a gastric cavity.

FIG. 5 shows a third embodiment of the device, in which the first internal cavity (5) of the chamber (1) is made up of three sectors connected to each other through two respective narrowings (10). This embodiment results in a chamber (1) that is even more flexible and adaptable.

Figures 6, 7:
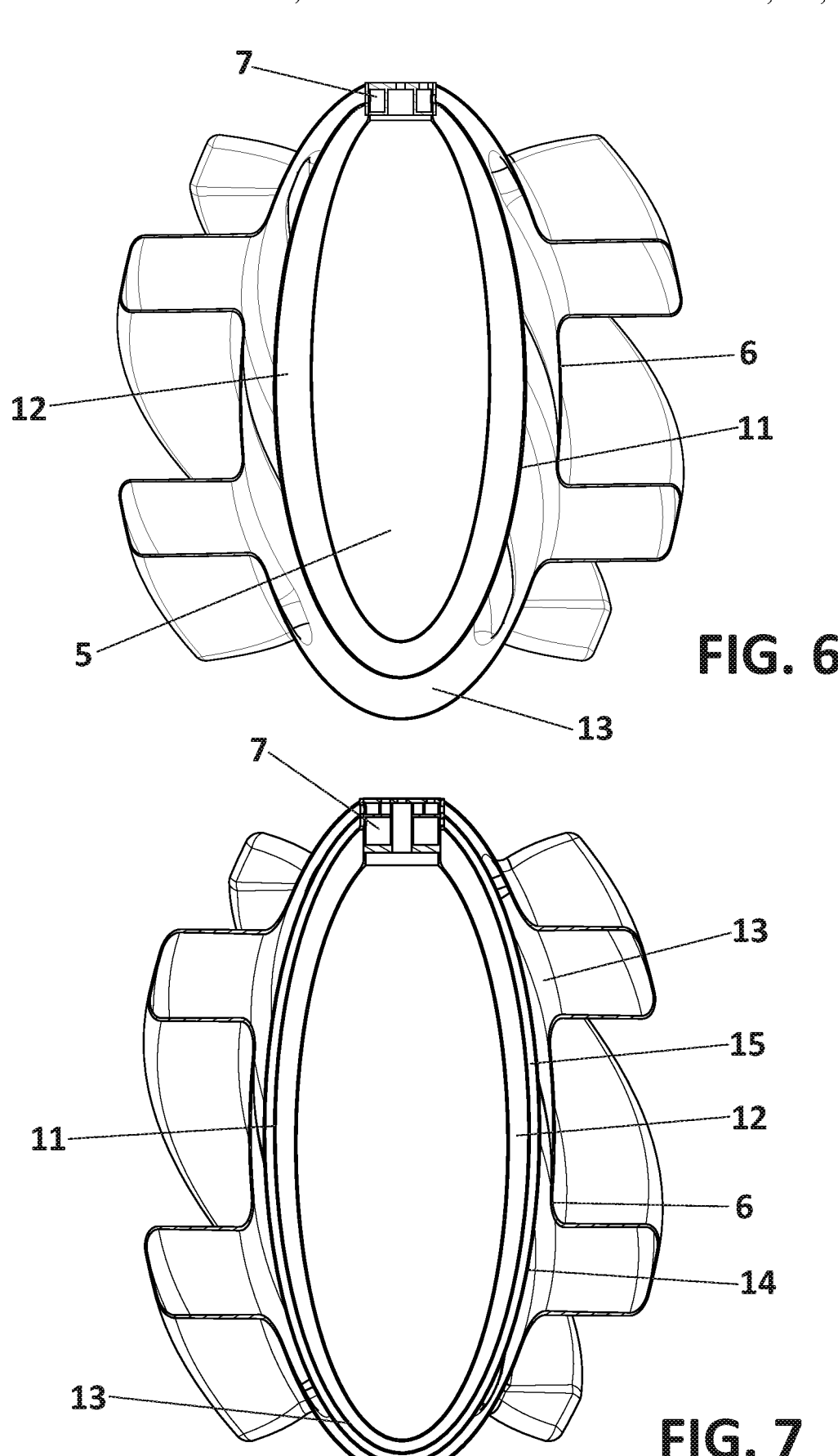
FIG. 6.—Shows a cross section of the device according to a fourth embodiment.
FIG. 7.—Shows a cross section of the device according to a fifth embodiment.

FIG. 6 shows a fourth embodiment of the device, in which the covering (2) additionally comprises a first flexible inner membrane (11) for dividing the second cavity (8) into an inner sector (12) and an outer sector (13). Said first inner membrane (11) runs in a direction essentially parallel to the inner face of the second wall (6).

The inner sector (12) is bounded between the outer face of the first wall (3) and one face of the first inner membrane (11), while the outer sector (13) is bounded between the opposite face of the first inner membrane (11) and the inner face of the second wall (6), thus including the thickenings (9).

In this fourth embodiment, the second valve (7) comprises two separate fluid conduits, for independent introduction of the fluid inside the internal sector (12) and the external sector (13) of the second cavity (8).

FIG. 7 shows a fifth embodiment of the device, in which the covering (2) further comprises, in addition to the first inner membrane (11), a second flexible inner membrane (14) for additional division of the second cavity (8) in an intermediate sector (15) located between the inner sector (12) and the outer sector (13).

In this fifth embodiment, the second valve (7) comprises three separate fluid conduits for independent introduction of fluid into the internal sector (12), the external sector (13) and the intermediate sector (15) of the second cavity (8).

Figures 8, 9:
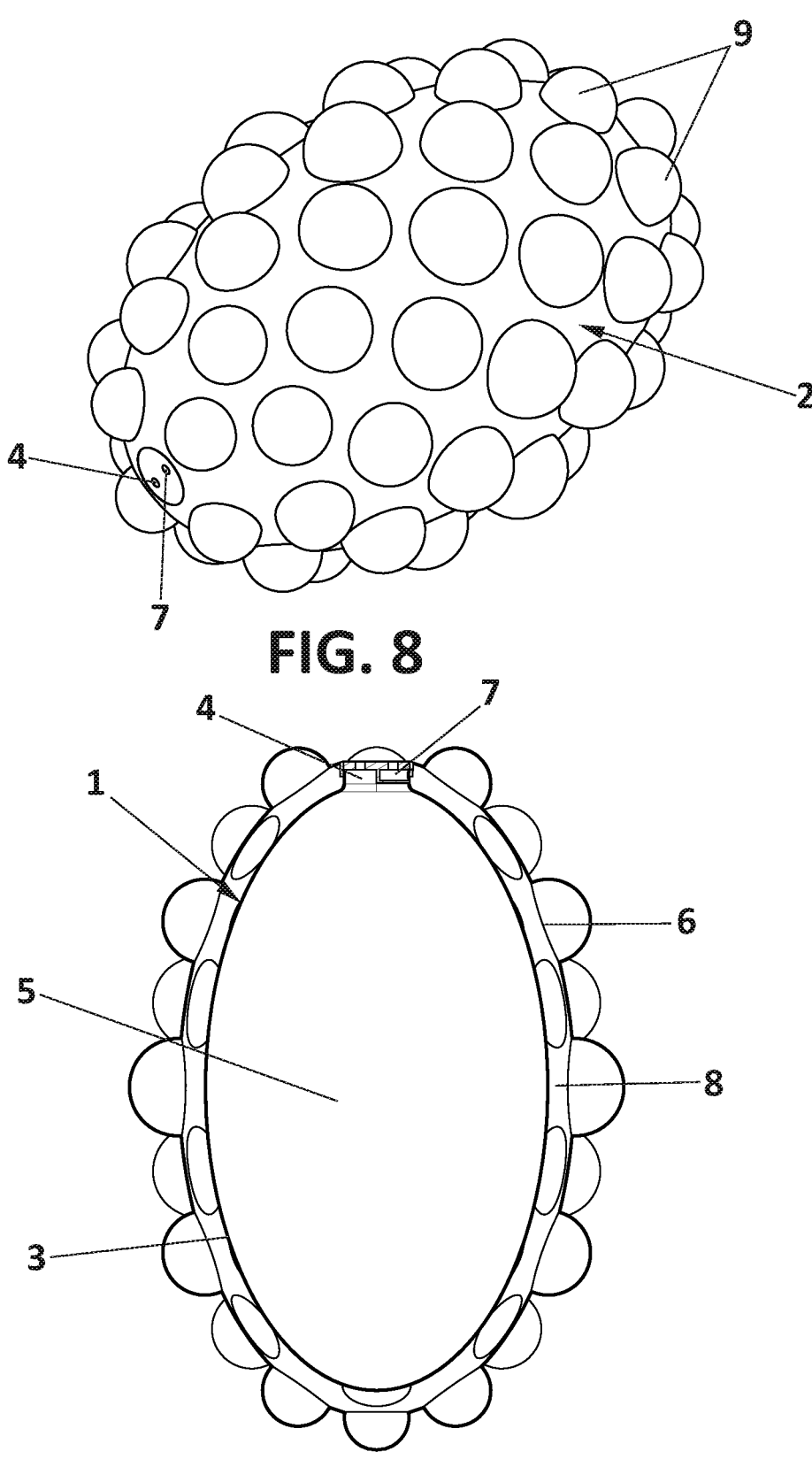
FIG. 8.—Shows a perspective view of the intragastric device according to a sixth preferred embodiment.
FIG. 9.—Shows a cross section of the device in FIG. 8.
Figure 10:
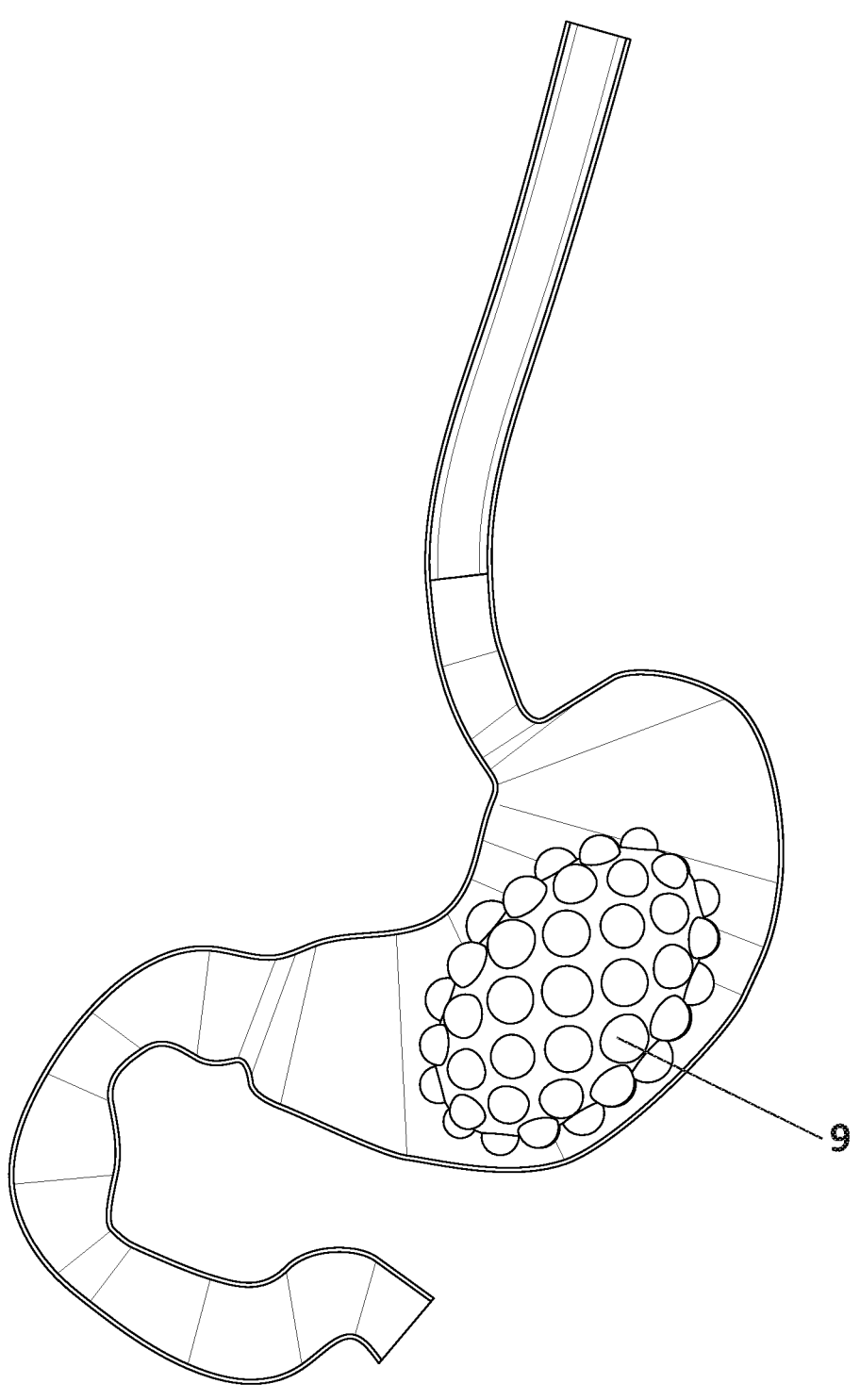
FIG. 10.—Shows the device of FIG. 8 inserted inside a gastric cavity.

FIGS. 8-10 illustrate views of the intragastric device according to a sixth preferred embodiment. As can be seen, in this embodiment, the thickening (9) of the covering (2) has a geometry in the form of hemispherical bubbles that start from the external face of the second wall (6) and project outwards from the device. These thickenings (9), whose volume is adjustable by means of the fluid introduced and extracted through the second valve (7), help to facilitate the adaptation of the device to the interior of the gastric cavity in which it is intended to be inserted.

Figure 11:
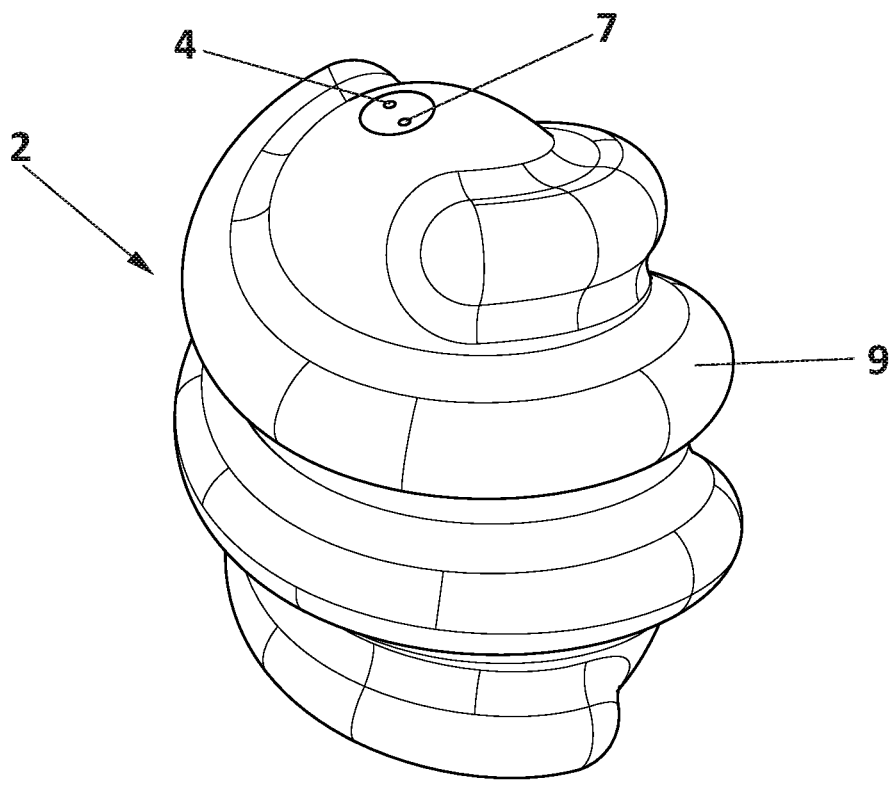
FIG. 11.—Shows a perspective view of the intragastric device according to a seventh preferred embodiment.
Figure 12:
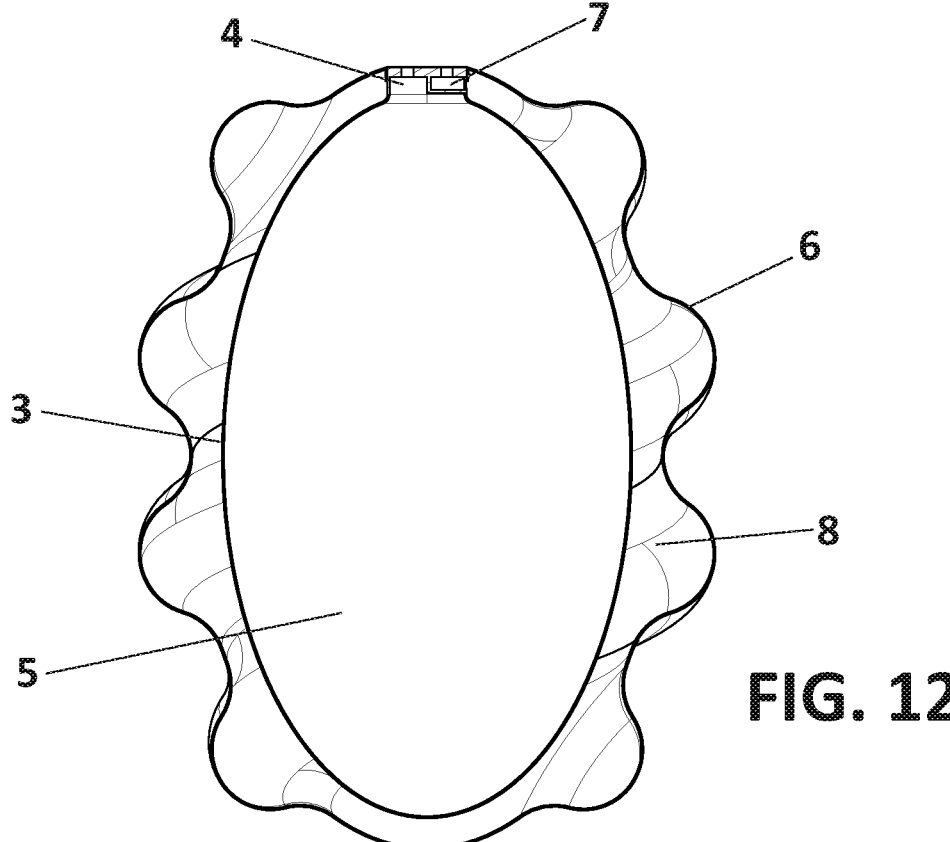
FIG. 12.—Shows a cross section of the device in FIG. 11.
Figure 13:
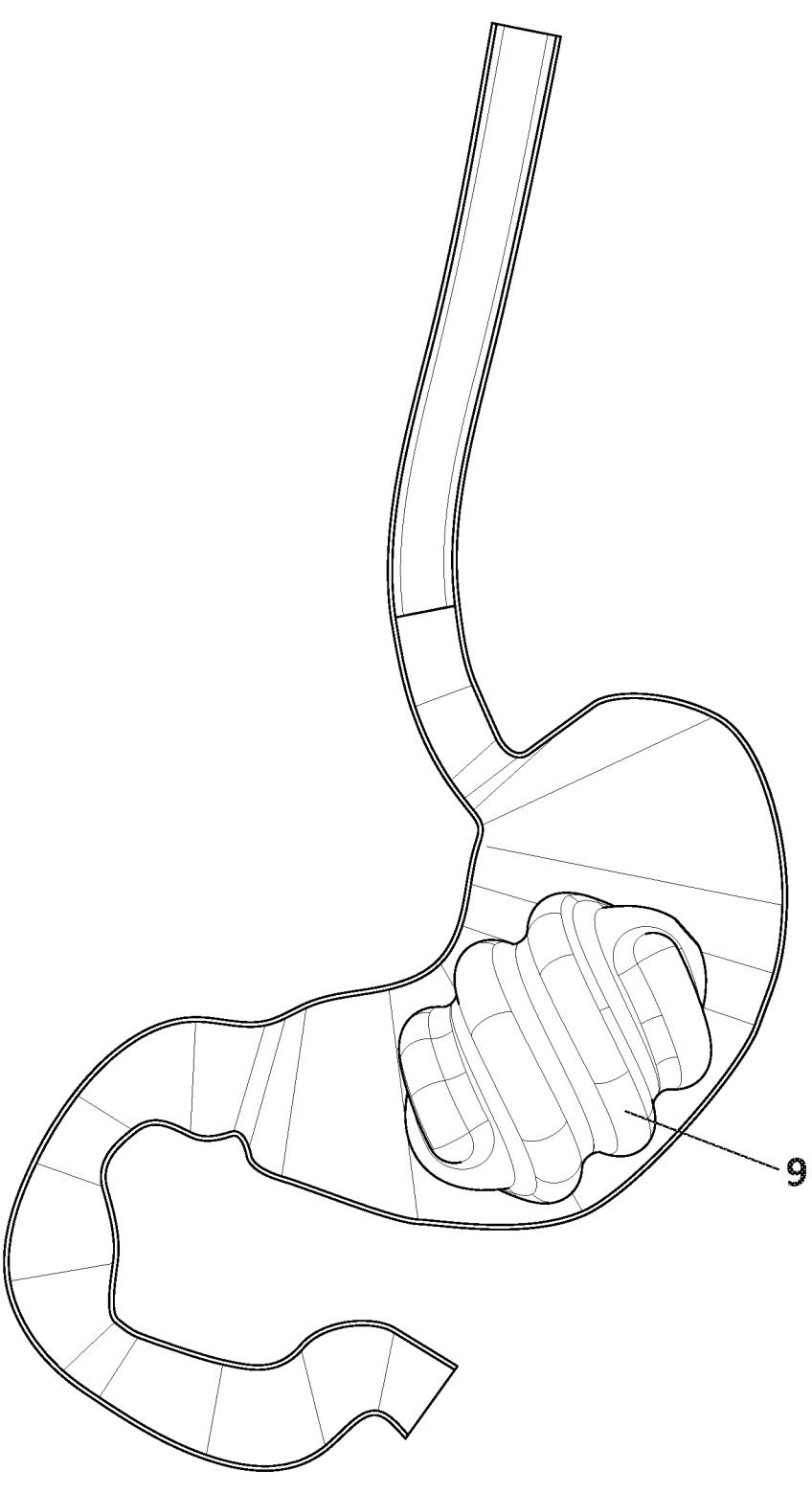
FIG. 13.—Shows the device of FIG. 11 inserted inside a gastric cavity.

Finally, FIGS. 11-13 show views of the intragastric device according to a seventh preferred embodiment. As can be seen, in this embodiment, the thickening (9) of the covering (2) has a spiral geometry that starts from the outer face of the second wall (6) and projects outwards from the device. As in the other cases, the volume of these spiral thickening (9) can be regulated by the fluid introduced and extracted through the second valve (7).

In an alternative embodiment of the intragastric device, not shown in the accompanying figures, the thickenings (9), whatever their geometry, are physically separated from the second cavity (8) by a membrane. Their volume is regulated by the introduction of fluid through a third valve, independent of the first valve (4) and the second valve (7).

In this alternative embodiment and in the case of the hemispherical thickening (9), these would be connected to each other through a plurality of channels for fluid circulation from the third valve.

In a last embodiment of the device, not shown in the attached figures, the external face of the second wall (6) of the covering (2) is flat and does not present the thickening (9) mentioned above, leaving the surface of the device smooth.

Figures 14, 15:
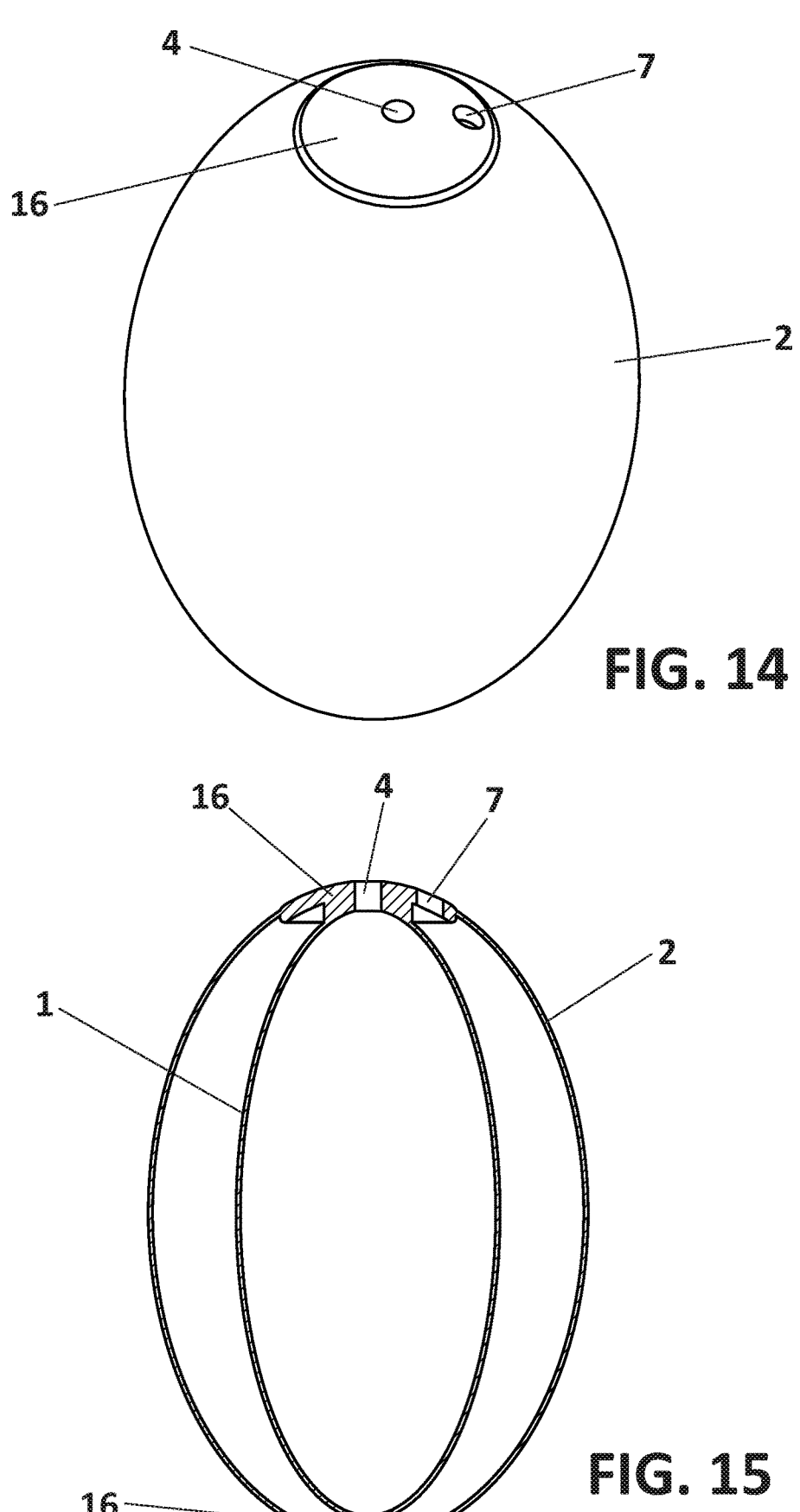
FIG. 14.—Shows a perspective view of the intragastric device according to an eighth preferred embodiment.
FIG. 15.—Shows a cross section of the device in FIG. 14.

In an alternative embodiment of the device, the inner chamber (1) and the outer covering (2) are joined together at at least two connection points (16). As can be seen in the attached FIGS. 14-15, the two connection points (16) are preferably located in the area of the valves (4,7) and at the opposite end to the valves (4,7).

The invention claimed is:

1. An intragastric device, insertable into a gastric cavity to restrict food intake capacity, comprising an ellipsoidal and flexible inner chamber, comprising:

a first wall, curved and closed on itself, with an external face and an internal face, which perimetrically delimits a first hollow internal cavity;

a first valve connecting the inside of the first cavity to the outside of the device; and a flexible outer covering, which at least partially sur-
rounds and contains the chamber and which in turn
comprises:
  a second wall, curved and closed on itself, with an
    external face, intended to face the internal walls of
    the gastric cavity, and an internal face that delimits
    perimetrically a second cavity that houses inside it
    the first wall and part of the first valve of the
    chamber, and
  a second valve connecting the inside of the second
    cavity to the outside of the intragastric device;
wherein the first cavity houses a volume of pressurized
  fluid introduced into and extracted from through the
  first valve, and the second cavity houses a volume of
  pressurized fluid introduced into and extracted from
  through the second valve, wherein the fluid pressure of
  the pressurized fluid inside the second cavity is differ-
  ent from the fluid pressure of the pressurized fluid
  inside the first cavity; and
wherein the first internal cavity of the chamber is made up
  of sectors connected to each other by means of nar-
  rowings.
2. Intragastric device according to claim 1, wherein:
the covering further comprises a first flexible inner mem-
  brane for dividing the second cavity into:
  an inner sector bounded between the outer face of the
    first wall and a face of the first inner membrane, and
  an outer sector bounded between the opposite side of
    the first inner membrane and the inner side of the
    second wall, and
    the second valve comprises two separate fluid pas-
      sages for independent introduction of the fluid into
      the inner and outer sectors of the second cavity.
3. Intragastric device according to claim 2, wherein:
the covering comprises a second flexible inner membrane
  for additional division of the second cavity in an
  intermediate sector located between the inner sector
  and the outer sector, and
the second valve comprises three separate fluid passages
  for independent introduction of fluid into the inner
  sector, the outer sector and the intermediate sector of
  the second cavity.

4. Intragastric device according to claim 3, wherein the
covering incorporates a plurality of thickenings which, start-
ing from the outer face of the second wall, project outwards
from the device.
5. Intragastric device according to claim 4, wherein the
thickenings have helical geometry.
6. Intragastric device according to claim 4, wherein the
thickenings have spiral geometry.
7. Intragastric device according to claim 4, wherein the
thickenings have hemispherical bubble geometry.
8. Intragastric device according to claim 4, wherein the
thickenings are connected to the second cavity.
9. Intragastric device according to claim 4, wherein:
the thickenings are physically separated from the second
  cavity by a membrane, and
the device incorporates a third valve for independent
  introduction of fluid into the interior of the thickenings.
10. Intragastric device according to claim 7, wherein the
hemispherical thickenings are connected to each other
through a plurality of channels for fluid circulation from the
third valve.
11. Intragastric device according to claim 1, wherein the
fluid introduced is a gas and/or a liquid.
12. Intragastric device according to claim 1, wherein the
inner chamber and the outer covering are solidly linked at
least two attachment points.
13. Intragastric device according to claim 12, wherein the
two attachment points are located in the area of the valves
and at the opposite end of the valves.
14. Intragastric device according to claim 1, wherein the
covering incorporates a plurality of thickenings which, start-
ing from the outer face of the second wall, project outwards
from the device.
15. Intragastric device according to claim 2, wherein the
covering incorporates a plurality of thickenings which, start-
ing from the outer face of the second wall, project outwards
from the device.
16. Intragastric device according to claim 9, wherein the
hemispherical thickenings are connected to each other
through a plurality of channels for fluid circulation from the
third valve.
17. Intragastric device according to claim 10, wherein the
fluid introduced is a gas and/or a liquid.

* * * * *